US011673925B2

(12) United States Patent
Wang et al.

(10) Patent No.: US 11,673,925 B2
(45) Date of Patent: Jun. 13, 2023

(54) OLIGOPEPTIDE WITH ANTI-INFLAMMATORY ACTIVITY, PREPARATION METHOD, AND APPLICATION THEREOF

(71) Applicants: NANJING UNIVERSITY OF FINANCE AND ECONOMICS, Nanjing (CN); NANJING UNIVERSITY OF CHINESE MEDICINE, Nanjing (CN)

(72) Inventors: Fang Wang, Anqing (CN); Xinchun Shen, Nanjing (CN); Yong Fang, Nanjing (CN); Zebin Weng, Nanjing (CN)

(73) Assignees: NANJING UNIVERSITY OF FINANCE AND ECONOMICS, Nanjing (CN); NANJING UNIVERSITY OF CHINESE MEDICINE, Nanjing (CN)

( * ) Notice: Subject to any disclaimer, the term of this patent is extended or adjusted under 35 U.S.C. 154(b) by 0 days.

(21) Appl. No.: 17/811,302

(22) Filed: Jul. 7, 2022

(65) Prior Publication Data
US 2023/0008335 A1 Jan. 12, 2023

(30) Foreign Application Priority Data
Jul. 8, 2021 (CN) .......................... 2021107740933

(51) Int. Cl.
| | | |
|---|---|---|
| *C07K 14/415* | (2006.01) | |
| *A23L 33/18* | (2016.01) | |
| *A23L 33/00* | (2016.01) | |
| *A61P 29/00* | (2006.01) | |
| *A61K 8/64* | (2006.01) | |
| *A61Q 19/00* | (2006.01) | |
| *A61K 38/00* | (2006.01) | |

(52) U.S. Cl.
CPC ............ *C07K 14/415* (2013.01); *A23L 33/18* (2016.08); *A23L 33/40* (2016.08); *A61K 8/645* (2013.01); *A61P 29/00* (2018.01); *A61Q 19/00* (2013.01); *A23V 2002/00* (2013.01); *A61K 38/00* (2013.01)

(58) Field of Classification Search
None
See application file for complete search history.

(56) References Cited

FOREIGN PATENT DOCUMENTS

CN 108165595 A * 6/2018 ............... C07K 1/34

OTHER PUBLICATIONS

Conner et al. Inflammation, Free Radicals, and Antioxidants. Nutrition. 1996; 12: 274-277. (Year: 1996).*

* cited by examiner

*Primary Examiner* — Aradhana Sasan
*Assistant Examiner* — Jia-Hai Lee
(74) *Attorney, Agent, or Firm* — WPAT, P.C

(57) ABSTRACT

An oligopeptide with anti-inflammatory activity, a preparation method, and an application thereof are provided, belonging to the field of biotechnology. An amino acid sequence of the oligopeptide is shown as SEQ ID NO:1. The preparation method includes: digesting a wheat germ protein through a simulated gastrointestinal tract to obtain protein digestion products; separating the protein digestion products by ultrafiltration membranes to obtain components I (>3 kDa), II (1~3 kDa), and III (<1 kDa), screening the components to obtain III as an anti-inflammatory active component, and finally identifying the oligopeptide by LC-MS/MS polypeptide. The oligopeptide has strong anti-inflammatory activity, is derived from the wheat germ protein, has the characteristics of safety, high efficiency, simple preparation method, good repeatability, has broad prospects in food, medicine, and other fields, and can be applied to preparations of medicines or functional foods for preventing and treating enteritis.

3 Claims, 4 Drawing Sheets

Specification includes a Sequence Listing.

OLIGOPEPTIDE WITH ANTI-INFLAMMATORY ACTIVITY, PREPARATION METHOD, AND APPLICATION THEREOF

TECHNICAL FIELD

The disclosure relates to biotechnologies, more particular to an oligopeptide with anti-inflammatory activity, a preparation method of the oligopeptide, and an application/use thereof.

STATEMENT REGARDING SEQUENCE LISTING

The sequence listing associated with this application is provided in text format in lieu of a paper copy and is hereby incorporated by reference into the specification. The name of the XML file containing the sequence listing is 22012THXT-USP1-2022-0014-SL.xml. The XML file is 2,177 bytes; was created on Jul. 7, 2022; contains no new matter; and is being submitted electronically via EFS-Web.

BACKGROUND

Inflammation is an adaptive immune response, which is a host defense against damaged tissues or infectious pathogens Inflammation is closely related to a variety of diseases, especially chronic inflammation, including asthma, inflammatory bowel disease, cancer, type II diabetes, lipid metabolism disorders, cardiovascular diseases (e.g., hypertension and hyperlipidemia), and central nervous system related diseases (e.g., Parkinson's disease and cognitive disorder). The incidence of these chronic inflammatory diseases is increasing year by year, which has become a health hazard of universal concern all over the world. Inflammation is a normal host defense response to stimulation by damage factors, which is a complex regulatory process involving multiple cells (e.g., macrophages, lymphocytes, monocytes, etc.) and multiple factors (signal transduction and activated transcription factors, vasoactive amines, cytokines, chemokines, and inflammation related enzymes).

Wheat germ is a by-product of wheat processing, which is rich in a variety of nutrients and is a natural plant protein with abundant production and wide sources. There is a lack of oligopeptides derived from natural substances, with high safety and strong anti-inflammatory activity in the art.

SUMMARY

A purpose of the disclosure is to provide an oligopeptide with strong anti-inflammatory activity, which is derived from a wheat germ protein and has the characteristics of high safety and wide sources.

Another purpose of the disclosure is to provide a preparation method of the oligopeptide, which is simple, safe, efficient and has good repeatability.

Still another purpose of the disclosure is to provide an application/use of the oligopeptide in preparing at least one selected form a medicine, a cosmetic, and a functional food with anti-inflammatory activity.

The purposes of the disclosure are realized by technical solutions as follows.

Specifically, an oligopeptide with anti-inflammatory activity is provided, and its amino acid sequence is shown as SEQ ID NO:1.

The disclosure also provides a preparation method of the oligopeptide, including the following steps: (1) digesting a wheat germ protein through a simulated gastrointestinal tract to obtain protein digestion products; and (2) taking the protein digestion products and separating the protein digestion products by an ultrafiltration membrane to obtain a component, and taking the component with a molecular weight less than 1 kilodalton (kDa), to thereby obtain the oligopeptide.

In an embodiment of the disclosure, the wheat germ protein in the step (1) is extracted from defatted wheat germ powder by using an alkaline-extraction and acid-precipitation method (also referred to as alkali extraction and acid precipitation).

In an embodiment of the disclosure, the digesting a wheat germ protein through a simulated gastrointestinal tract described in the step (1) includes the following steps: digesting the wheat germ protein with pepsin first to obtain intermediate digestion products (also referred to as simulated gastric digestion products), and then digesting the intermediate digestion products with trypsin and α-chymotrypsin, to thereby obtain wheat germ protein digestion product.

In an embodiment of the disclosure, a digestion time of the pepsin is in a range of 3-5 hours (h), a digestion time of the trypsin and α-chymotrypsin is in range of 5-7 h.

In an embodiment of the disclosure, a pore size of the ultrafiltration membrane in the step (2) is a length that allows a passage of the component with the molecular weight less than 1 kDa.

The disclosure also provides an application of the oligopeptide in preparing at least one of a medicine, a cosmetic, and a functional food with anti-inflammatory activity, and the medicine, the cosmetics, or the functional food contains the oligopeptide.

The oligopeptide can reduce the secretion of inflammatory factors and can be used as medicines or functional foods for preventing and treating enteritis. The oligopeptide of the disclosure is separated from the wheat germ protein. Through the determination of the nitric oxide (NO) content of macrophages induced by lipopolysaccharide (LPS) in vitro and the secretion of inflammatory factors, it is concluded that the oligopeptide with the amino acid sequence as shown in SEQ ID NO:1 not only has no effect on the proliferation activity of macrophages, but also can reduce the secretion of proinflammatory cytokines (also referred to as inflammatory factors) interleukin-1 beta (IL-1β), interleukin-6 (IL-6), and tumor necrosis factor alpha (TNF-α) of the LPS induced macrophages and increase the secretion of anti-inflammatory factor interleukin-10 (IL-10). Therefore, the oligopeptide has strong anti-inflammatory activity and can be applied to the preparation of anti-inflammatory medicines, cosmetics, or functional products, and has broad prospects in the field of foods, medicines, and cosmetics. The oligopeptide of the disclosure is derived from the wheat germ protein, so that the safety is higher; and its preparation method is simple, easy to operate and wide in source.

DETAILED DESCRIPTION OF EMBODIMENTS

Figure 1:
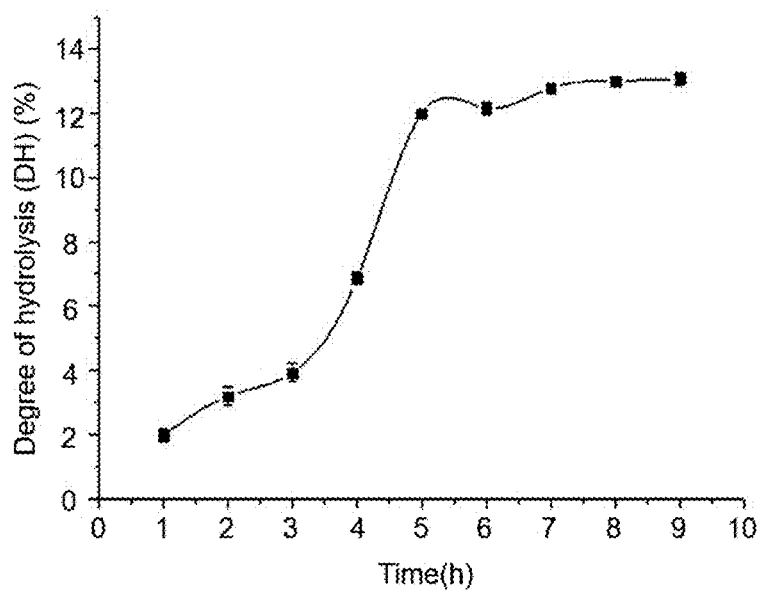
FIG. 1 shows changes of degrees of hydrolysis of a wheat germ protein at different digestion times, where an abscissa is the digestion time and an ordinate is the degree of hydrolysis.

Experimental methods used in the following embodiments are conventional methods unless otherwise specified.

Materials and reagents used in the following embodiments are commercially available unless otherwise specified.

1. Materials: an oligopeptide derived from a wheat germ protein used in the experiment is synthesized by Genscript Biotechnology Co., Ltd. using FlexPeptide™ peptide synthesis technology according to liquid chromatography with tandem mass spectrometry (LC-MS/MS) identification results, and its sequence is shown as SEQ ID NO: 1. Trypsin (2500 active units per microgram, abbreviated as U/mg) is obtained from Sangon Biotech (Shanghai) Co., Ltd. Pepsin (3000 U/mg) is obtained from Beijing Solarbio Science & Technology Co., Ltd. RAW 264. 7 cell line is obtained from Beijing Center for Disease Prevention and Control (CDC). Fetal bovine serum (FBS), Roswell Park Memorial Institute (RPMI) 1640 culture medium, Penicillin-Streptomycin (100×), Trypsin EDTA (0.05%), and Hank's Balanced Salt Solution (HBSS, Gibco™) are obtained. A fluorescent probe 2,7-Dichlorodihydrofluorescein diacetate (DCFH-DA) and dimethyl sulfoxide (DMSO) (Sigma-Aldrich®) are obtained. Nitric oxide (NO) kits, enzyme-linked immunosorbent assay (ELISA) kits (including tumor necrosis factor alpha abbreviated as TNF-α, interleukin-1 abbreviated as IL-1, interleukin-6 abbreviated as IL-6, and interleukin-10 abbreviated as IL-10), microprotein assay (Bicinchoninic Acid abbreviated as BCA method) kits (obtained from Nanjing Jiancheng Bioengineering Institute). Other reagents are analytical reagent from China.

2. Main instruments and equipment include: a biological safety cabinet (obtained from Thermo Fisher Scientific (China) Co., Ltd.); a MZE multifunctional microplate reader (also referred to as multi-mode plate reader or multi-detection plate reader, which is obtained from Molecular Devices, LLC.); a SL16R desktop centrifuge (also referred to as laboratory centrifuge, which is obtained from Thermo Fisher Scientific (China) Co., Ltd.); a carbon dioxide ($CO_2$) incubator (obtained from Thermo Fisher Scientific (China) Co., Ltd.); and a fluorescence microscope (obtained from Carl Zeiss GmbH, Germany).

Embodiment 1 Preparation of an Oligopeptide with Anti-Inflammatory Activity (1) extraction of a wheat germ protein. Specifically, wheat germs degreased by n-hexane (its molecular formula is $C_6H_{14}$) are crushed by a pulverizer (also referred to as crusher) and then sieved through a 100-mesh sieve to obtain sieved parts as wheat germ powder. 500 milliliters (mL) distilled water and 100 mL sodium chloride (NaCl) aqueous solution (containing 5 grams (g) NaCl) are added into 50 g wheat germ powder to obtain a mixture, the mixture is adjusted to pH 9.0 with sodium hydroxide (NaOH) aqueous solution, stirred with a magnetic stirrer for 30 minutes (min), and then centrifuged at 4 Celsius degrees (° C.) and 5000 revolution per minutes (r/min) for 10 min to thereby obtain a supernatant. The supernatant is taken and adjusted to pH 4.0 with hydrochloric acid, and centrifuged for 10 min after a large white precipitate appears. The precipitate is taken, dissolved with distilled water, and adjusted to pH 7 with NaOH aqueous solution. After dialysis and desalination, wheat germ protein powder is obtained by vacuum freeze drying and stored at −20° C. for further use.

(2) wheat germ protein simulated gastrointestinal tract digestion. Specifically, the wheat germ protein powder is dissolved first with deionized water and stirred evenly to obtain a wheat germ protein solution with a mass percentage concentration of 8%. The wheat germ protein solution is heated in 95° C. water bath for 30 min, and adjusted to pH 7.0 to completely denature the protein. The completely denatured wheat germ protein solution is adjusted to pH 2.0 with hydrochloric acid, pepsin (3000 U/mg; purchased from Beijing Solarbio Science & Technology Co., Ltd., Cat. No. P8390) with 0.4% of wheat germ protein mass is added for digestion at 37° C. for 4 hours (h) to obtain thereby intermediate digestion products. Then, the intermediate digestion products are adjusted to pH 7.6 with sodium hydroxide aqueous solution, trypsin (purchased from Sangon Biotech (Shanghai) Co., Ltd., t.No.T0785, 2500 U/mg) with 0.3% wheat germ protein mass is added, then α-chymotrypsin (purchased from Beijing Solarbio Science & Technology Co., Ltd., Cat.No.C8660, 1200 U/mg) is added, and digested at 37° C. for 6 h. During digestion, samples are collected every 1 h to determine a degree of hydrolysis (DH) and a peptide yield. After 10 h, the solution after digestion and hydrolysis is cooled to room temperature, then centrifuged at 5000 r/min for 20 min to collected a supernatant. The supernatant is dialyzed and desalted, and vacuum freeze-dried, a wheat germ protein digestion product is obtained.

As shown in FIG. 1, during the simulated gastrointestinal tract digestion process of wheat germ protein, the degree of hydrolysis of wheat germ protein shows an overall upward trend with the increase of digestion time. During the simulated gastric digestion stage (pepsin), the wheat germ protein begins to hydrolyze, and the degree of hydrolysis is 1.96%-

6.87% in 0-4 h. After trypsin and α-chymotrypsin are added to the simulated intestinal digestion stage, the degree of hydrolysis increases sharply, and then the degree of hydrolysis increases slowly and tends to be stable, and finally the DH reaches 13.08%.

(3) separation and purification of the wheat germ protein digestion product. Specifically, ultrafiltration membranes with cut-off molecular weights of 3 kilodaltons (kDa) and 1 kDa are selected. The wheat germ protein digestion product is prepared into a 0.1% mass concentration solution using a phosphate buffer at a concentration of 0.1 Moles per liter (M), pH 7.6, and insoluble matters are removed by filtration through a 0.45 micrometers (μm) cellulose membrane. The wheat germ protein digestion product solution is separated by a LabScale small volume Tangential Flow Filter (TFF) system. Firstly, the ultrafiltration membrane with the cut-off molecular weight of 3 kDa is selected for separation to obtain a component with a molecular weight greater than 3 kDa (recorded as component WGPH-I) and components with a molecular weight less than or equal to 3 kDa. Then, the components with a molecular weight less than or equal to 3 kDa are separated by the ultrafiltration membrane with the cutoff molecular weight of 1 kDa to obtain a component with a molecular weight greater than or equal to 1 kDa but less than or equal to 3 kDa (recorded as component WGPH-II) and a component each with a molecular weight less than 1 kDa (recorded as component WGPH-III). During ultrafiltration, a pump pressure is 0.2 megapascals (MPa), an ultrafiltration temperature is 4° C.

The components with different molecular weights WGPH-I (>3 kDa), WGPH-II (1~3 kDa), and WGPH-III (<1 kDa) obtained after ultrafiltration are desalted and freeze-dried. The effects of respective components on the proliferation activity of RAW 264.7 normal macrophages are detected. In addition, the effects of WGPH-I (>3 kDa), WGPH-II (1~3 kDa), and WGPH-III (<1 kDa) on the nitric oxide (NO) production of RAW 264.7 macrophages induced by lipopolysaccharide (LPS) are detected to evaluate the anti-inflammatory activity of oligopeptide.

(4) detection of effects of respective components (WGPH-I, WGPH-II, and WGPH-III) on the proliferation activity of RAW 264.7 normal macrophages by a methyl thiazolyl tetrazolium (MTT) assay RAW 264.7 macrophages in a logarithmic growth phase are taken and prepared into a cell suspension of $3\times10^4$ cells/mL in a RPIM 1640 culture medium containing 10% FBS. Sample wells are set in a 96-well plate (also referred to as 96-well tissue culture plates), and 100 microliters (μL) of cell suspension are added to each sample well, and the cells are cultured in a cell incubator for 12 h to make the cells adhere to the wall. After removing the culture medium in the sample wells, different components WGPH-I (>3 kDa), WGPH-II (1~3 kDa), and WGPH-III (<1 kDa) are dissolved in RPIM 1640 culture medium containing 10% FBS to prepare different concentrations of oligopeptide culture medium (0, 50, 100, 200, and 300 μg/mL) respectively, and then added to respective sample wells, 100 μL per well. A blank well is set, and compared with the sample wells, there is no cell, with 100 μL PBS instead of the oligopeptide culture medium. A control well is set, compared with the sample wells, there is cells, with 100 μL PBS instead of oligopeptide culture medium. After 96-well plate is cultured in the cell incubator at 37° C. for 2 h, 10 μL of 1 μg/mL LPS aqueous solution is added to each well. After the culture is continued for 24 h, 10 μL of MTT solution (5 mg/mL) is add to each well, and then the solution in the 96-well plate is removed after 4 h of culture. 50 μL DMSO is added to each well and oscillated in a constant temperature oscillation box at 37° C. for 20 min. The absorbance is measured at a wavelength of 570 nanometers (nm) in the microplate reader.

Cell proliferation activity=(optical density $(OD)_{sample\ well}-OD_{blank\ well})/(OD_{control\ well}-OD_{blank\ well})\times100\%$.

Figure 2:
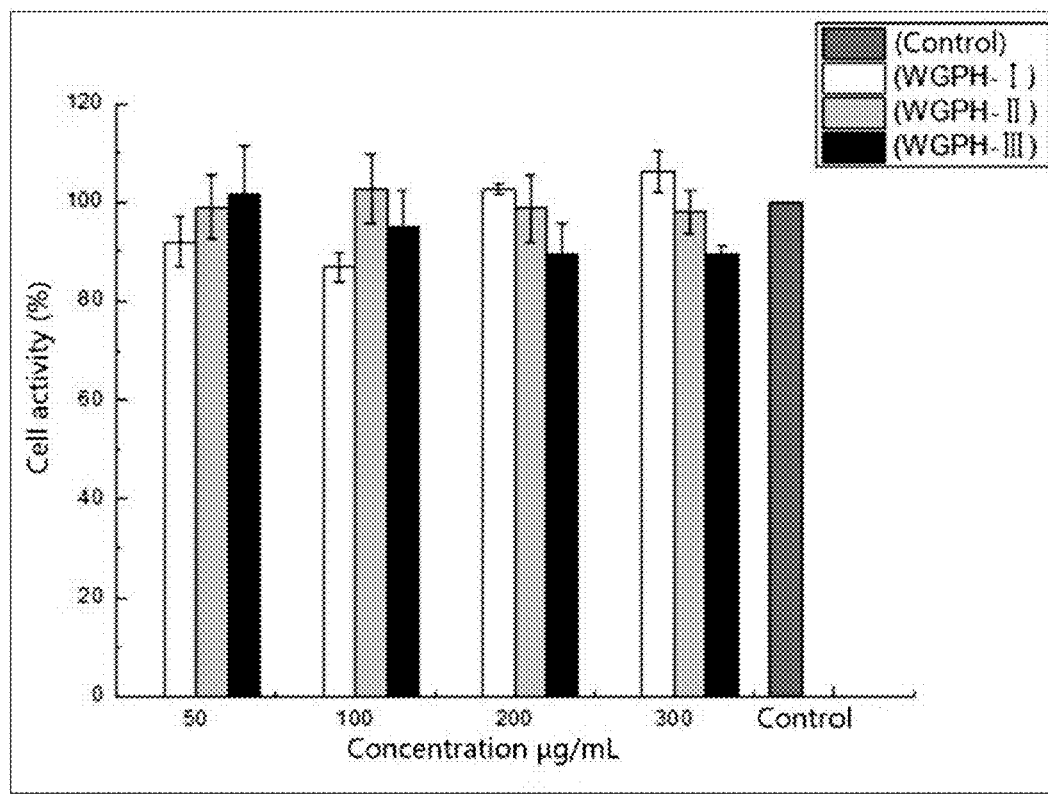
FIG. 2 shows effects of wheat gluten protein hydrolysates (WGPH)-I, WGPH-II, and WGPH-III on the proliferation activity of RAW 264.7 macrophages; where a control group is a control well, and WGPH-I, WGPH-II, and WGPH-III are sample wells added with WGPH-I, WGPH-II, and WGPH-III respectively.

As shown in FIG. 2, after 24 h treatment of each oligopeptide, there is no significant difference in absorbance with the increase of oligopeptide concentration, indicating that different components WGPH-I (>3 kDa), WGPH-II (1~3 kDa), and WGPH-III (<1 kDa) have no effect on the activity of macrophages. It indicates that components WGPH-I, WGPH-II, and WGPH-III are safe.

(5) detection of NO content of LPS induced RAW 264.7 macrophages by using a Griess method Effects of WGPH-I, WGPH-II, and WGPH-III on NO secretion of LPS induced RAW 264.7 macrophages are detected by a NO detection kit (purchased from Nanjing Beyotime Institute of Biotechnology). Specific steps are as follows. RAW 264.7 macrophages in a logarithmic growth phase are taken and prepared into a cell suspension of $3\times10^4$ cells/mL with RPMI 1640 culture medium containing 10% (volume percentage concentration) FBS (fetal bovine serum). Sample wells are set in a 96-well plate, 100 μL of cell suspension is added to each sample well, then cultured in a carbon dioxide ($CO_2$) incubator for 12 h to make the cells adhere to the wall, and 100 μL of oligopeptide culture media with different concentrations (0, 20, 80, and 320 millimoles per liter (μM)) are added to respective sample wells after removing the culture medium in the sample wells. A control well and a model well are set in the 96-well plate. Compared to the sample wells, only difference is that PBS of the same volume is used to replace the oligopeptide culture medium. After the 96-well plate is cultured in the incubator at 37° C. for 2 h, 10 μL of 1 μg/mL LPS (lipopolysaccharide, Sigma-Aldrich®, USA) aqueous solution is added to each well of the sample wells and the model well, and cultured in the incubator at 37° C. for 24 h without adding LPS aqueous solution into the blank well. 50 μL supernatant is extracted from each well of the 96-well plate and transferred to each well of another 96-well plate, and then Griess I and Griess II solutions from the NO detection kit are added to each well in turn and mixed well. The absorbance value is detected by the microplate reader at 540 nm and then converted to a NO molar concentration. Among them, the oligopeptide culture media with different concentrations (0, 20, 80, and 320 μM) are obtained by dissolving oligopeptide in RPMI 1640 containing 10% FBS.

Figure 3:
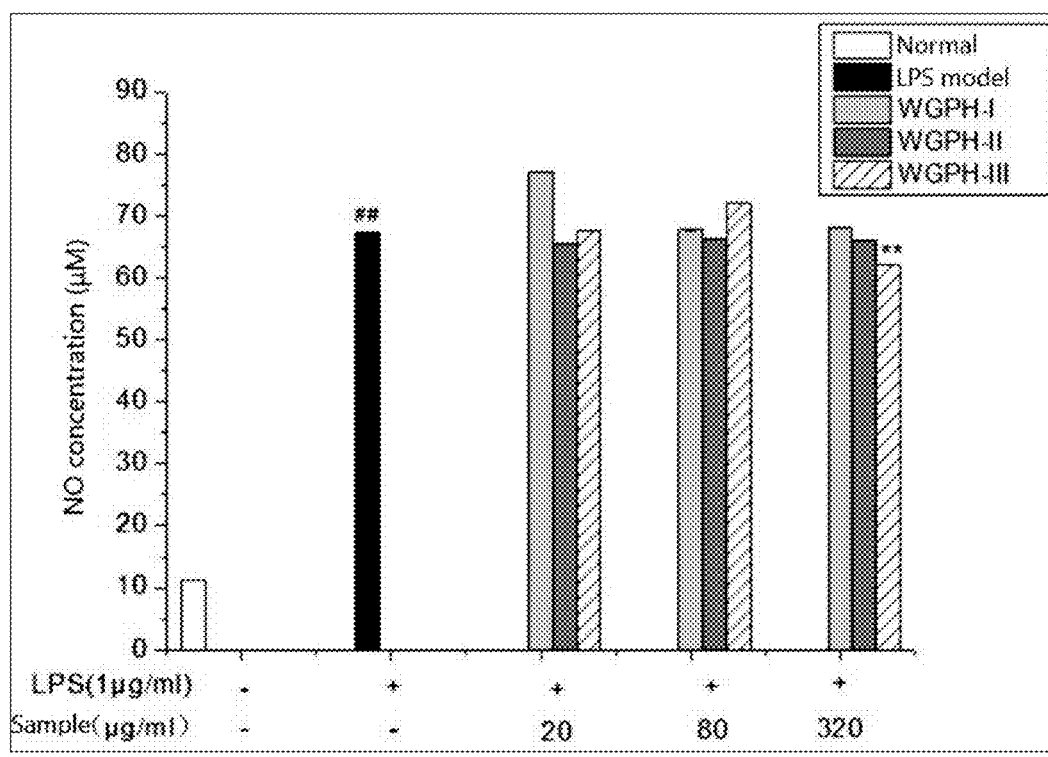
FIG. 3 shows effects of WGPH-I, WGPH-II and WGPH-III on the nitric oxide (NO) production of the RAW 264.7 macrophages induced by lipopolysaccharide (LPS); where a blank group is a blank well, a LPS model group is a model well, and WGPH-I, WGPH-II and WGPH-III are sample groups added with WGPH-I, WGPH-II or WGPH-III respectively; and where ##represents a very significant difference compared with the blank well ($p<0.01$), and **represents a very significant difference compared with the model well ($p<0.01$).

As shown in FIG. 3, there is no significant difference between the NO concentration of the cells intervened by WGPH-II and WGPH-I and the NO concentration of the cells in the model well. The NO concentration of in cells intervened by the component WGPH-III decreases significantly with significant difference, indicating that the component WGPH-III can significantly reduce the NO secretion of macrophages induced by LPS and has certain anti-inflammatory activity.

Figure 4:
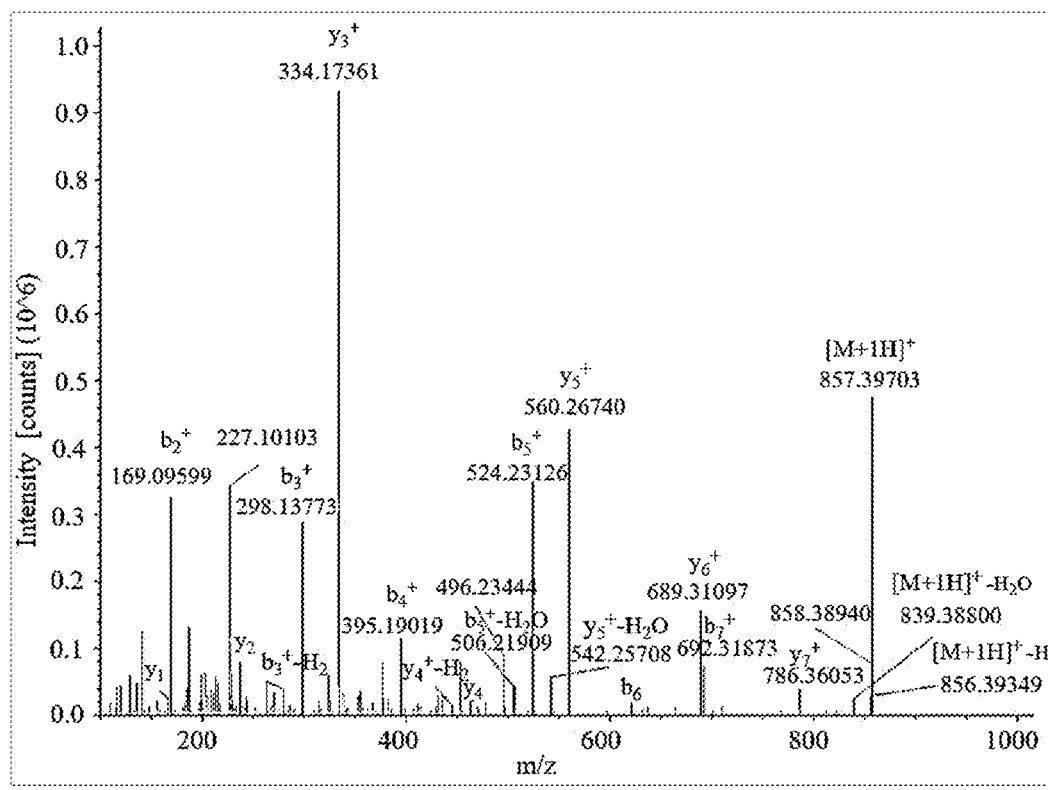
FIG. 4 shows a secondary mass spectrum (also referred to as secondary ion mass spectrometry, abbreviated as SIMS) of the oligopeptide, where an abscissa is a mass-to-charge ratio (m/z) of ions and an ordinate is an intensity of ion flow.
Figure 5A:
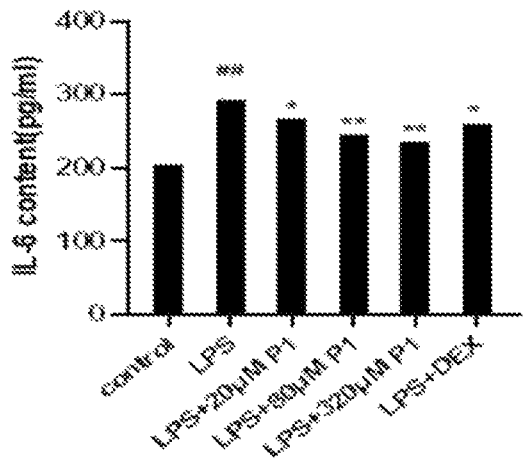
FIGS. 5a-5d show effects of the oligopeptide on the secretion of inflammatory factors of the RAW 264.7 macrophages; where control represents a blank well, LPS represents a LPS model well, LPS+ respective concentrations P1" respectively represent sample wells of LPS induced cells and intervened with oligopeptide of the respective concentrations (where P1 is an abbreviation of oligopeptide), and LPS+DEX (DEX is an abbreviation of dexamethasone) represents a positive well; and where # represents that the LPS model well has a significant difference compared with the blank well ($p<0.05$), ##represents that the LPS model well has a very significant difference compared with the blank well ($p<0.01$),*represents that the sample well or the positive well has a significant difference compared with the LPS model well ($p<0.05$), **represents that the sample well or the positive well has a very significant difference compared with the LPS model well ($p<0.01$).
Figure 5B:
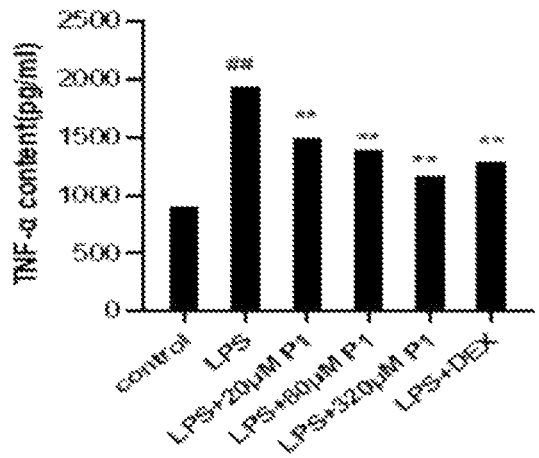
Figure 5C:
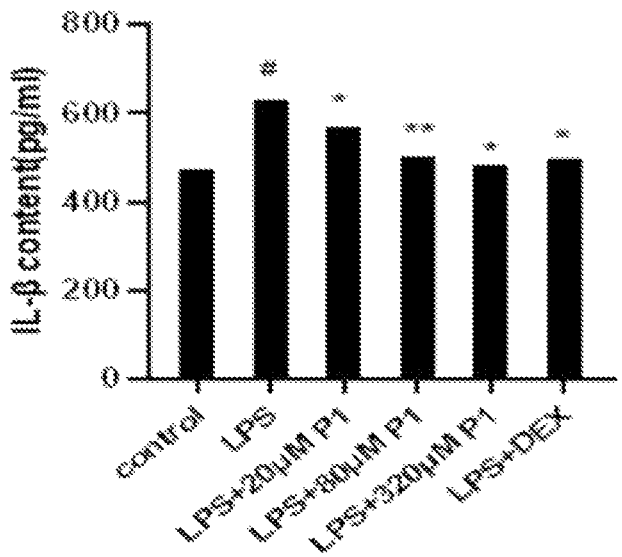
Figure 5D:
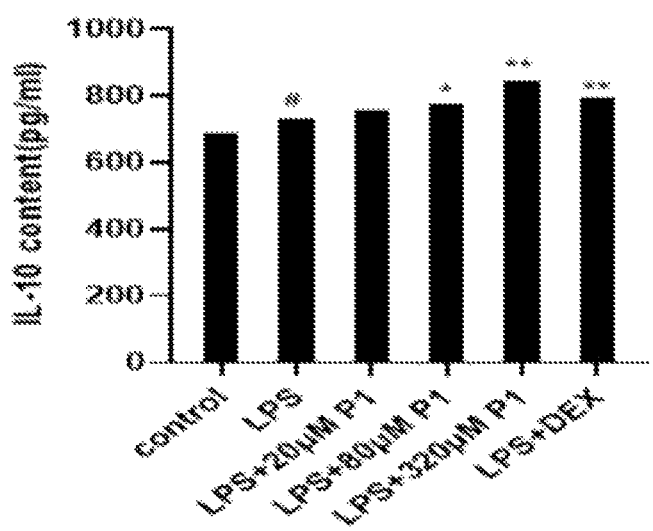

(6) structure identification. Specifically, the purity of active component and amino acid sequence in WGPH-III are determined by LC-MS/MS. The component WGPH-III is freeze-dried to obtain WGPH-III freeze-dried powder. The WGPH-III freeze-dried powder is dissolved in deionized water to prepare a protein solution with a concentration of 20 μg/mL. A mobile phase A is a formic acid aqueous solution with a mass percent concentration of 0 1%, a mobile phase B is a formic acid acetonitrile solution with a mass percent concentration of 0.1%, and a BEH C18 chromatographic column is selected. A elution procedure is as follows: 0-5 min, 100~85% linear decrease of the mobile phase A, 0~15% linear increase of the mobile phase B; and 5-10 min, 85~100% linear increase of the mobile phase A, 15%~0 linear decrease of the mobile phase B. The percentage in the elution procedure is the volume percentage concentration. After the sample passes through the liquid chromatography separation system, peptide segments are broken into fragments with different molecular weights by the mass spectrometry system, and ionic fragments are separated by the mass analyzer according to the mass number, and the mass spectrum is obtained by the detector. The experimental results are shown in FIG. 4. By analyzing the mass spectrum, it is found that the active component in WGPH-III is an oligopeptide with the amino acid sequence shown as SEQ ID NO: 1, with a molecular weight of 856.92 Da and a mass percentage being greater than or equal to 98%.

(7) determination of anti-inflammatory activity of the oligopeptide

The oligopeptide is synthesized by Genscript Biotechnology Co., Ltd. using FlexPeptide™ peptide synthesis technology (the amino sequence is shown as SEQ ID NO: 1) for the following experiments.

The effect of oligopeptide intervention on inflammatory factors in LPS induced RAW 264.7 macrophages is detected. A specific detection method includes steps as follows. RAW 264.7 macrophages in the logarithmic growth phase are taken and prepared $3\times10^4$ cells/mL cell suspension in RPMI 1640 culture medium containing 10% (volume percentage concentration) FBS. Sample wells are set in a 24 well plate, 400 μL of the cell suspension is added into each sample well, then cultured in a $CO_2$ incubator for 12 h to make the cells adhere to the wall, and oligopeptide culture media with different concentrations (0, 20, 80, 320 μM) are added respectively. The 24-well plate is also provided with a blank well, a LPS model well, and a positive well. Compared with the sample wells, the blank well and the LPS model well are different only in that no oligopeptide culture medium is added, and the difference between the positive well and the sample well is that the positive well contains 100 μM of dexamethasone (DEX) culture medium (where the solvent is RPMI 1640 culture medium containing 10% FBS) for replacing the oligopeptide culture medium. After the 24-well plate is cultured in the incubator for 2 h, 10 μL of 1 μg/mL LPS solution is added to each well of the sample wells, the LPS model well, and the positive well, not added to the blank well, and then the 24-well plate is placed in the incubator for 24 h at a constant temperature. The ELISA kit (TNF-α, IL-1, IL-6, and IL-10) (purchased from Hangzhou MultiSciences (Lianke) Biotech Co., Ltd.) is used to detect the contents of the inflammatory factors IL-1β, IL-6, IL-10, and TNF-α. Among them, the oligopeptide culture media with different concentrations (0, 20, 80, 320 μM) are obtained by dissolving the oligopeptide in RPMI 1640 culture medium containing 10% (volume percentage concentration) FBS.

As shown in FIGS. 5a-5d, in 320 μM of the oligopeptide intervened cells, the concentration of IL-6 is 79.19% of that of the cells in the LPS model well, the concentration of IL-1β is 78.91% of that of the cells in the LPS model well, the concentration of is 61.36% of that of the cells in the LPS model well, and the concentration of IL-10 anti-inflammatory factor is 1 14 times of that of the cells in the LPS model well. three hundred and twenty μ Compared with the cells treated with the positive medicine DEX, in the 320 μM of the oligopeptide intervened cells, the concentrations of IL-6, IL-1β, and TNF-α are 94%, 98% and 95% of that of the cells in the positive well respectively, and the concentration of IL-10 is 1.01 times of that of the cells in the positive well.

Compared with the blank well, the secretion of the proinflammatory cytokines IL-6, TNF-α, and IL-1β in LPS-induced cells is significantly increased (p<0.05), but when the oligopeptide is interfered with different concentrations, the secretion of the proinflammatory cytokines IL-6, TNF-α, and IL-1β is significantly inhibited (p<0.05) compared with that of the LPS model well. The secretion of IL-10 is significantly increased after LPS treatment compared with the blank well (p<0.05), and the secretion of IL-10 of the cells treated with the oligopeptide with a concentration of 20 μM has no significant difference compared with the LPS model well (p>0.05). When the sample wells are added with the oligopeptide with the concentrations of 80μ M and 320 μM, the secretion of IL-10 shows an increasing trend, which is very significantly different from that of the LPS model well (p<0.01). Therefore, the results show that the oligopeptide could reduce the secretion of the proinflammatory cytokines IL-1β, IL-6, and TNF-α of LPS induced macrophages, and increase the secretion of anti-inflammatory factor IL-10.

In conclusion, the oligopeptide of the disclosure has good anti-inflammatory activity, can reduce the LPS induced RAW 264.7 macrophages and increase the secretion of anti-inflammatory factor IL-10.

---

SEQUENCE LISTING

```
Sequence total quantity: 1
SEQ ID NO: 1           moltype = AA  length = 8
FEATURE                Location/Qualifiers
REGION                 1..8
                       note = wheat germ protein
source                 1..8
                       mol_type = protein
                       organism = synthetic construct
SEQUENCE: 1
APEPEPAF                                                                8
```

What is claimed is:

1. An oligopeptide with anti-inflammatory activity, consisting of the amino acid sequence of the SEQ ID NO: 1.

2. An application method of the oligopeptide according to claim 1, comprising:
   preparing a product with anti-inflammatory activity by using the oligopeptide, wherein product is at least one selected from a medicine, a cosmetic, and a functional food.

3. A product, comprising at least one selected from a medicine, a cosmetic, and a functional food, wherein the product contains the oligopeptide according to claim 1.

* * * * *